US012791475B2

(12) United States Patent

Alessandri et al.

(10) Patent No.: US 12,791,475 B2

(45) Date of Patent: Nov. 10, 2026

(54) METHOD FOR CHARACTERIZING A BIOLOGICAL MICROTISSUE USING IMAGING

(71) Applicant: TREEFROG THERAPEUTICS, Pessac (FR)

(72) Inventors: Kevin Alessandri, Bordeaux (FR); Pierre Bon, Villenave D'Ornon (FR)

(73) Assignee: TREEFROG THERAPEUTICS, Pessac (FR)

(*) Notice: Subject to any disclaimer, the term of this patent is extended or adjusted under 35 U.S.C. 154(b) by 302 days.

(21) Appl. No.: 17/914,041

(22) PCT Filed: Mar. 26, 2021

(86) PCT No.: PCT/EP2021/057977

§ 371 (c)(1),
(2) Date: Sep. 23, 2022

(87) PCT Pub. No.: WO2021/191433

PCT Pub. Date: Sep. 30, 2021

(65) Prior Publication Data

US 2023/0122507 A1 Apr. 20, 2023

(30) Foreign Application Priority Data

Mar. 27, 2020 (FR) .................................. FR2003036

(51) Int. Cl.

*G01N 21/45* (2006.01)
*C12M 1/12* (2006.01)

(Continued)

(52) U.S. Cl.

CPC ............. *G01N 21/45* (2013.01); *C12M 25/02* (2013.01); *C12M 41/00* (2013.01); *C12M 41/46* (2013.01);

(Continued)

(58) Field of Classification Search

CPC . G01N 21/45; G01N 2021/451; C12M 25/02; C12M 41/00; C12M 41/46; G02B 21/0056

See application file for complete search history.

(56) References Cited

U.S. PATENT DOCUMENTS 9,482,659 B2 * 11/2016 Loewke ............. G01N 33/4833
9,557,549 B2 * 1/2017 Yaqoob ................ G02B 21/365

(Continued)

FOREIGN PATENT DOCUMENTS

FR 3059009 A1 5/2018
FR 3108623 A1 10/2021

(Continued)

OTHER PUBLICATIONS

Ledwig, epi-mode tomographic quantitative phase imaging, optical society of america, 2019 (Year: 2019).*

(Continued)

*Primary Examiner* — Dominic J Bologna

(74) *Attorney, Agent, or Firm* — Greer, Burns & Crain, Ltd.

(57) ABSTRACT

The invention relates to a method for in vitro characterization of a eukaryote biological microtissue by imaging by means of a phase measurement technique without a reference beam, and the use of this method in vitro characterization in particular for:

monitoring the quality of a microtissue,
measuring the increase of the biomass of a microtissue during its growth and/or its amplification
following the differentiation and/or the organization of a microtissue during its maturation,
determining the phenotype of cells of the microtissue, and/or (Continued)

confirming the absence of non-differentiated cells in the microtissue.

26 Claims, 5 Drawing Sheets

(51) Int. Cl.
*C12M 1/34* (2006.01)
*G02B 21/00* (2006.01)

(52) U.S. Cl.
CPC ... *G02B 21/0056* (2013.01); *G01N 2021/451* (2013.01)

(56) References Cited

U.S. PATENT DOCUMENTS

| | | | | |
|---|---|---|---|---|
| 2014/0375792 | A1* | 12/2014 | Yaqoob | G01N 21/453 348/79 |
| 2016/0367146 | A1* | 12/2016 | Boppart | A61B 5/7207 |
| 2018/0113064 | A1 | 4/2018 | Allier et al. | |
| 2019/0284722 | A1* | 9/2019 | Soliman | C12N 5/0663 |
| 2019/0302000 | A1* | 10/2019 | Lo | G01J 3/0229 |
| 2019/0330589 | A1 | 10/2019 | Feyeux et al. | |
| 2020/0096941 | A1 | 3/2020 | Tatsuta et al. | |

FOREIGN PATENT DOCUMENTS

| | | | | |
|---|---|---|---|---|
| JP | 2023519906 | A | 5/2023 | |
| WO | WO-2018096277 | A1 * | 5/2018 | A01N 1/0284 |
| WO | 2021191433 | A1 | 9/2021 | |

OTHER PUBLICATIONS

Maji, Development of gelatin, Carbohydrate Polymers, 2018 (Year: 2018).*
Chin, Epithelial Cell Chirality, PNAS, 2018 (Year: 2018).*
Soto, Label-free quantitative 3D tomographic imaging, Optics Express, 2017 (Year: 2017).*
Osten, Recent advances in digital holography, Applied Optics, 2014 (Year: 2014).*
Hu, Higher order transport of intensity equation methods, IEEE Photonics Journal, 2019 (Year: 2019).*
Bon, Quadriwave lateral shearing interferometry, Optics Express, 2009 (Year: 2009).*
Wang, Spatial light interference microscopy, Optical Society of America, 2011 (Year: 2011).*
Descloux, Combined multi-plane phase retrieval and super-resolution, nature photonics, 2018 (Year: 2018).*
Zangle, Live-cell mass profiling, Nature Methods, 2014 (Year: 2014).*
Bon, Self-interference 3D super-resolution microscopy for deep tissue investigations, Nature Methods, 2018 (Year: 2018).*
Zuppinger, 3D culture for cardiac cells, Biochimica et Biophysica Acta, 2016 (Year: 2016).*
Huisken, Jan, and Didier YR Stainier. "Selective plane illumination microscopy techniques in developmental biology." (2009): 1963-1975 (Year: 2009).*
Soto, Juan M., José A. Rodrigo, and Tatiana Alieva. "Optical diffraction tomography with fully and partially coherent illumination in high numerical aperture label-free microscopy." Applied Optics 57.1 (2017): A205-A214. (Year: 2017).*
Soto, Juan M., José A. Rodrigo, and Tatiana Alieva. "Label-free quantitative 3D tomographic imaging for partially coherent light microscopy." Optics express 25.14 (2017): 15699-15712 (Year: 2017).*
Bon, Pierre, et al. "Self-interference 3D super-resolution microscopy for deep tissue investigations." Nature methods 15.6 (2018): 449-454. (Year: 2018).*
Robles, F., "Epi-mode tomographic quantitative phase imaging in thick scattering samples", Progress in Biomedical Optics and Imaging, SPIE—International Society for Optical Engineering, Bellingham, Feb. 20, 2020, pp. 112511Y-112511Y, vol. 11251, No. 20.
Hu, J., et al., "Higher Order Transport of Intensity Equation Methods: Comparisons and Their Hybrid Application for Noise Adaptive Phase Imaging", IEEE Photonics Journal, Jun. 3, 2019, vol. 11, No. 3.
Bon P., et al., "Self-interference 3D super-resolution microscopy for deep tissue investigations", Nature Methods, Jun. 2018, pp. 449-454, vol. 15, No. 6.
Vellekoop, I., et al, "Digital optical phase conjugation of fluorescence in turbid tissue", Applied Physics Letters, Aug. 20, 2012, pp. 81108-81108, vol. 101, No. 8.
Bon, P., et al., "Quadriwave lateral shearing interferometry for quantitative phase microscopy of living cells", Optics Express, Jul. 20, 2009, p. 13080-13094, vol. 17, No. 15.
Osten, G., et al., "Recent advances in digital holography [Invited]", Applied Optics, Jul. 30, 2014, pp. G44, vol. 53, No. 27.
Aknoun, S. et al., "Living cell dry mass measurement using quantitative phase imaging with quadriwave lateral shearing interferometry: an accuracy and sensitivity discussion", Journal of Biomedical Optics, vol. 20, No. 12, Dated Dec. 1, 2015, pp. 126009-1 to 126009-15.
Barty, A. et al., "Quantitative optical phase microscopy", Optics Letters, vol. 23, Issue 11, dated Jun. 1, 1998, pp. 817-819.
Berto, P. et al., "Wavefront sensing with a thin diffuser", Optics Letters, vol. 42, Issue 24, Compiled Oct. 12, 2017, pp. 5117-5120.
Chung, Y. et al., "Human embryonic stem cell lines generated without embryo destruction", Cell Stem Cell, vol. 2, No. 2, dated Feb. 7, 2008, pp. 113-117.
Descloux, A. et al., "Combined multi-plane phase retrieval and super-resolution optical fluctuation imaging for 4D cell microscopy", Nature Photonics, vol. 12, No. 3, Mar. 2018, pp. 165-172.
Gong, H. et al., "Optical path difference microscopy with a Shack-Hartmann wavefront sensor", Optics Letters, vol. 42, No. 11, dated Jun. 1, 2017, pp. 2122-2125.
Nakagawa, M. et al., "Generation of Induced Pluripotent Stem Cells Without Myc From Mouse and Human Fibroblasts", Nature Biotechnology, Jan. 1, 2008, vol. 26, No. 1, pp. 101-106.
Park, Y. et al., "Quantitative phase imaging in biomedicine", Nature Photonics, vol. 12, Oct. 2018, pp. 578-589.
Parthasarathy, A.B. et al., "Quantitative phase imaging using a partitioned detection aperture", Optics Letters vol. 37, Issue 19, dated Oct. 1, 2012, pp. 4062-4064.
Shahbazi, M.N., et al., "Self-organization of the human embryo in the absence of maternal tissues", Nature Cell Biology, vol. 18, No. 2, Published online May 4, 2016, pp. 24.
Soto, J.M. et al., "Label-free quantitative 3D tomographic imaging for partially coherent light microscopy", Optics Express, vol. 25, Issue 14, dated Jul. 10, 2017, pp. 15699-15712.
Takahashi, K., et al., "Induction of Pluripotent Stem Cells From Adult Human Fibroblasts by Defined Factors", Cell, Nov. 30, 2007, vol. 131, No. 5, pp. 861-872.
Wang, Z. et al., "Spatial light interference microscopy (SLIM)", Optics Express vol. 19, Issue 2, published Jan. 7, 2011, pp. 1016-1026.
Yu, J., et al., "Induced Pluripotent Stem Cell Lines Derived from Human Somatic Cells", Science, Dec. 21, 2007, vol. 318, No. 5858, pp. 1917-1920.
Zangle, T.A. et al., "Live-cell mass profiling: an emerging approach in quantitative biophysics", Nature Methods, vol. 11, No. 12, Published online Nov. 25, 2014, pp. 1221-1228.
Zheng, G. et al., "Wide-field, high-resolution Fourier ptychographic microscopy", Nature Photonics, vol. 7, Sep. 1, 2013, pp. 739-745.
Zuppinger, C., "3D culture for cardiac cells", Biochimica et Biophysica Acta (BBA)—Molecular Cell Research, vol. 1863, Issue 7, Part B, Jul. 2016, pp. 1873-1881.
Preliminary research report and Written Opinion received in French Patent Application No. FR2003036, mailed on Dec. 4, 2020, 10 pages.

(56) References Cited

OTHER PUBLICATIONS

International Search Report and Written Opinion received in PCT Application No. PCT/EP2021/057977, mailed on Jun. 30, 2021, 24 pages. [English Translation submitted].

International Preliminary Report on Patentabillity received in PCT Application No. PCT/EP2021/057977, mailed on Sep. 22, 2022, 18 pages. [English Translation submitted].

* cited by examiner

METHOD FOR CHARACTERIZING A BIOLOGICAL MICROTISSUE USING IMAGING

CROSS-REFERENCE TO RELATED APPLICATIONS

This application is the U.S. national stage application of PCT/EP2021/057977 filed Mar. 26, 2021 and claiming the benefit of priority from French patent application FR2003036 filed Mar. 27, 2020, the entire disclosure of both applications is herein incorporated by reference in its entirety.

BACKGROUND

The present invention relates to the characterization, by imaging, of biological tissues, in particular biological microtissues.

In research and in treatment, it is essential to be able to characterize the living biological cells and tissues, in particular during or after a cell culture, in particular in order to monitor the cell proliferation and/or the quality of the cells and of the tissue, and/or in order to follow the differentiation of cells, and/or in order to follow the organization of the tissue, and/or in order to determine the phenotype(s) of the cells forming a tissue, etc.

However, the current imaging techniques, which are in particular those implementing fluorescence microscopy, histology, capacitance measurement, optical density, and standard transmission imaging, do not allow for this.

Fluorescence microscopy is used, coupled with fluorescent probes such as antibodies or endogenic fluorescence, by genetically modifying cells. A plurality of techniques using fluorescence microscopy are generally used, in particular confocal microscopy, light sheet microscopy (or SPIM for “Selective Plane Illumination Microscopy”), multiphotonic microscopy, flow cytometry (“FACS”). These techniques are well-established, but they require fixing (cell death) and/or limiting conditions (marking only of extracellular proteins), or are not compatible with the cell culture with the aim of cellular treatment, such as the addition of non-GMP destructive products or products which cause the genetic modification of cells. They are therefore not suitable for the characterization of living tissues because they are invasive, often destructive, and very slow.

The histology techniques consist in fixing and then marking the tissues. These again involve the destruction of cells and exhibit the same disadvantages as the fluorescence microscopy.

Measuring biomass by means of a capacitance probe proceeds from the principle that the living cells can be considered to be capacitors. This measurement thus takes into account only the accessible outside surface of cells having an integrated membrane. The case of aggregates of cells and microtissues is more complex and will depend on the tightness of connections between cells. In contrast with the previous methods, this is non-invasive, but it makes it possible to have information merely on the only inaccessible volume or on the surface of this volume, which is too limiting and imprecise for the characterization of tissues.

The standard transmission imaging techniques, such as quantitative phase contrast, are rapid and non-invasive. The phase measurement in imaging is a measurement of the local delay of a light beam after interaction with the object studied. The devices used for the phase imaging are based on the phenomenon of optical interference for encoding the phase information into luminous intensity information. Various phase imaging techniques for microscopy are described in particular in (Park, Y., Depeursinge, C. & Popescu, G. Quantitative phase imaging in biomedicine, Nature Photon 12, 578-589 (2018) doi:10.1038/s41566-018-0253-x). Today, phase imaging is used for characterizing fine samples (isolated cells or microtissue slices of thicknesses less than 10 μm), but cannot be used for microtissues or larger tissues. Indeed, the techniques currently used in phase imaging do not allow for quantitative measurement of the phase in a tissue. They remain qualitative, and not quantitative, and can therefore be used only with difficulty for the characterization of thick objects.

Finally, the measurement of the optical density, obtained by phase measurements and allowing access to the mass of the sample, does not allow for characterization of tissues of a size larger than 10 μm.

The object of the invention is to overcome these various problems of the prior art, and to propose a solution for a method for in vitro characterization of living tissues which is complete, rapid and non-invasive and which makes it possible to characterize in particular living biological microtissues, in particular during or at the end of cell culturing, in research or in treatment.

SUMMARY OF THE INVENTION

According to the invention, the phase measurement as currently carried out on very fine cells and microtissues necessarily uses a reference beam which results in an absolute measurement which is not suitable because it does not make it possible to measure the mass and to quantify a certain number of parameters.

This is why, in order to achieve the object of the invention, the inventors have developed a method for in vitro characterization of a human, animal or vegetable biological microtissue, the smallest dimension of which is greater than or equal to 20 μm, said method consisting in using a phase measurement technique without a reference beam and which does not make use of fluorescent marking.

Indeed, according to the invention, only the phase measurement techniques without a reference beam, i.e, the direct measurement techniques, or indeed referred to as relative phase measurements, can function for characterizing microtissues, the smallest dimension of which is greater than or equal to 20 μm. Moreover, according to the invention it is important to manage the coherence of the beam used for the lighting. In particular, it is expedient for the coherence in the region of the sample, i.e. that of the speckle generated by the sample (microtissue), to be reduced—preferably the speckle contrast is less than 75% of a maximum unit contrast, yet more preferably 50%, ideally 10%. In practice, this reduction of the speckle is achieved by reducing the spatial coherence and/or the temporal coherence. The spatial coherence of the lighting should preferably be such that the digital illumination opening does not exceed 90%, yet more preferably 50%, ideally 25%, of the digital opening of the imaging system, so as to measure the parameters of the sample in a manner independent of the coherence of the beam.

Advantageously, the use of a phase measuring technique without a reference beam makes it possible to quantitatively characterize living biological microtissues at high speed, without destroying them or modifying them.

This makes it possible in particular to:

- measure the increase of the biomass of a microtissue during its growth and/or its amplification, determine the viability of the cells, monitor the quality of a microtissue, follow the differentiation and/or the organization of a microtissue during its maturation, determine the phenotype of cells of the microtissue, and/or confirm the absence of non-differentiated cells in the microtissue.

The invention thus also relates to the use of the characterization method, for these applications in particular.

BRIEF DESCRIPTION OF THE FIGURES

FIG. 5*c* (right-hand side) shows the same object acquired by means of multiphotonic microscopy. The cell nuclei are marked by 10 ug/mL Hoechst 33342 (Thermofisher). Approximately half of the cells are visible. The total number of cells is approximately 500.

DEFINITIONS

Figure 1:
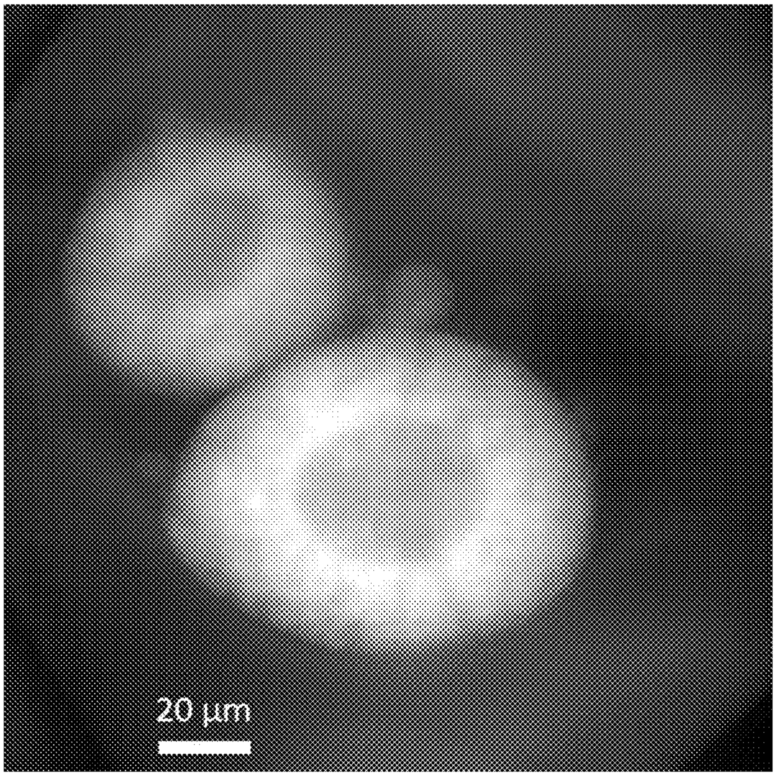
FIG. 1 is an image of hydrogel capsules containing human cells induced to pluripotency, obtained by imaging by phase measurement without a reference beam, according to the protocol described in the example.

"Local absorption" of the microtissue within the meaning of the invention means the attenuation of the light due to a local photon loss by absorption of the light and not diffusion.

Within the meaning of the invention, "alginate" means linear polysaccharides formed from β-D-mannuronate and α-L-guluronate, and salts and derivatives thereof.

Within the meaning of the invention, "hydrogel capsule" means a three-dimensional structure formed from a matrix of polymer chains swollen by a liquid, preferably water.

Within the meaning of the invention, "human cells" means human cells or cells of non-human mammals which are immunologically humanized. Even if this is not specified, the cells, the stem cells, the progenitor cells and the tissues according to the invention are made up of or are obtained from human cells or from cells of non-human mammals which are immunologically humanized.

Within the meaning of the invention, "progenitor cell" means a stem cell already engaged in cellular differentiation (for example in cells of the retina), but not yet differentiated. A progenitor cell is a cell which tends to be differentiated into a specific type of cell. It is therefore already more specific than a stem cell. The progenitor cells can divide only a limited number of times, being naturally subject to erosion of their telomeres.

Within the meaning of the invention, "embryonic stem cell" means a pluripotent stem cell derived from the internal cellular mass of the blastocyst. The pluripotency of embryonic stem cells can be evaluated by the presence of markers such as the transcription factors OCT4 and NANOG, and surface markers such as SSEA3/4, Tra-1-60 and Tra-1-81. The embryonic stem cells can be obtained without destroying the embryo from which they originate, for example by means of the technique described in Chang et al. (Cell Stem Cell, 2008, 2(2)): 113-117). Optionally, the embryonic stem cells of humans may be excluded.

Within the meaning of the invention, "pluripotent stem cell" or "pluripotent cell" means a cell which is capable of forming all the tissues present in the whole original organism, without, however, being able to form an entire organism per se. They may in particular be induced pluripotent stem cells, embryonic stem cells, or MUSE cells (for "Multilineage-differentiating Stress Enduring"). The pluripotent stem cells retain the length of their telomeres and can preserve the ability to divide without a clear limit of the number of cellular cycles, unlike progenitor cells.

Within the meaning of the invention, "induced pluripotent stem cell" means a pluripotent stem cell induced to pluripotency by genetic reprogramming of differentiated somatic cells. These cells are in particular positive for the pluripotency markers, such as the alkaline phosphatase coloration and the expression of the proteins NANOG, SOX2, OCT4 and SSEA3/4. Examples of methods making it possible to obtain induced pluripotent stem cells are described in the articles Yu et al. (Science 2007, 318 (5858): 1917-1920), Takahashi et al (Cell, 207, 131(5): 861-872) and Nakagawa et al (Nat Biotechnol, 2008, 26(1): 101-106).

Within the meaning of the invention, "differentiated" cells means cells which have a particular phenotype, in contrast with pluripotent stem cells which are not differentiated.

Within the meaning of the invention, "coherence" of the beam means the spatia-temporal coherence, i.e. the spatial extent and the spectral width of the illumination source.

Within the meaning of the invention, "density" of the microtissue means the mass of one unit volume divided by the mass of the same volume of culture medium.

Within the meaning of the invention, "microtissue" or "biological microtissue" means a biological tissue or a sample of biological tissue, the largest dimension of which is less than or equal to 1 cm.

Within the meaning of the invention, "phase" means the delay of the luminous wavefront, relative phase shift, and optical path difference between the environment of the microtissue and the base level of the medium into which it is plunged.

Within the meaning of the invention, "phase measurement technique" means any technique capable of quantitatively measuring the phase of the light.

Within the meaning of the invention, "phase measurement technique without a reference beam" means the techniques capable of going back to the phase component of the light, without having to resort to the use of an external beam, referred to as "reference," which has not interacted with the microtissue.

Within the meaning of the invention, "tissue" or "biological tissue" means the common sense of tissue in biology, i.e. the intermediate organization level between the cell and the organ. A tissue is a set of similar cells of the same origin (most often originating from a common cellular lineage, although they may originate by association of distinct cell lineages), grouped in a cluster, network or beam (fiber). A tissue forms a functional unit, i.e. the cells thereof contribute to the same function. The biological tissues regenerate regularly and are assembled together to form organs. A tissue may comprise differentiated cells and stem cells. Typically, the pluripotent stem cells form a tissue of the epithelia type, qualified as an epiblast (citation: Self-organization of the human embryo in the absence of maternal tissues, Shahbazi et al., Nat Cell Biol. 2016, doi: 10.1038/ncb3347).

Within the meaning of the invention, "texture" of a microtissue means the local roughness of the image and its local frequency content.

DETAILED DESCRIPTION

The invention thus relates to a method for in vitro characterization of a eukaryote biological microtissue, in particular a human, animal or vegetable microtissue, the smallest dimension of which is greater than or equal to 20 μm, even more preferably greater than or equal to 30 μm. The method consists in characterizing the biological microtissue in its entirety, and not only a portion of the microtissue.

The biological microtissue is preferably a microtissue, the largest dimension of which is less than or equal to 10 mm, even more preferably less than or equal to 1 mm, and in particular less than or equal to 500 μm, in particular less than or equal to 200 μm.

The biological microtissue may be a microtissue comprising eucaryote cells, in particular human cells, or animal (non-human) cells, in particular cells of amniotes and in particular cells of mammals, or vegetable cells.

When it is a human or animal microtissue, the biological microtissue may for example be selected from the epithelial, connective, muscular or nerve microtissues, According to an embodiment, the microtissue may in particular comprise:

differentiated cardiac cells or retinal cells or neural cells or cells of the liver or chondrocytes or keratinocytes or lymphoid cells, or hematopoietic stem cells or mesenchymal stem cells, and/or:

progenitor stem cells endothelial cells.

According to another embodiment, the microtissue may comprise or be made up of pluripotent cells in the form of an epiblast.

When it is a human or animal microtissue, the biological microtissue may, for example, be selected from the different phases of embryonic or fetal development, in particular the early phases of development within the context of in vitro fertilization for purposes of reproduction (in humans or animals) or research (in humans or animals), or animal production.

When it is a vegetable microtissue, the biological microtissue may, for example, be selected from the meristems, the parenchyma, the conducting tissues, the supporting tissues, the covering or protective tissues, the secretion tissues, and the nutritive tissues.

The microtissue may be surrounded, at least in part, by an extracellular matrix. The cellular matrix layer may be formed by the cellular matrix excreted by the cells of the microtissue and/or by the added extracellular matrix. The extracellular matrix layer may form a gel. It preferably comprises a mixture of proteins and extracellular compounds required for the growth of cells forming the microtissue. Preferably, the extracellular matrix comprises structural proteins, such as collagen, laminins, entactin, vitronectin, as well as growth factors, such as TGF-beta and/or EGF. The extracellular matrix layer may consist of or comprise Matrigel® and/or Geltrex® and/or a matrix of the hydrogel type of vegetable origin, such as modified alginates, or of synthetic origin, or of copolymer of poly(N-isopropylacrylamide) and polyethylene glycol) (PNIPAAm-PEG) of the Mebiol® type.

According to a variant, the microtissue may be a microtissue that is encapsulated in a microcompartment or a capsule comprising an external hydrogel layer, such as the microcompartments described in the patent application WO2018/096277. Reference is made to a hydrogel capsule. Preferably, the hydrogel used is biocompatible, i.e. it is not toxic for the cells. The hydrogel capsule must allow the diffusion of oxygen and of nutrients for feeding the cells contained in the microcompartment and to allow their survival. The external hydrogel layer may be an external layer comprising alginate. It may be formed exclusively of alginate. The alginate may in particular be a sodium alginate, made up of 80% α-L-guluronate and 20% β-D-mannuronate, having an average molecular mass of 100 to 400 kDa and a total concentration of between 0.5% and 5% by mass. The hydrogel capsule in particular makes it possible to protect the cells from the external medium and to limit the uncontrolled proliferation of cells.

The microtissue may be provided in any three-dimensional shape, i.e. it may be in the shape of any object in space. It may be provided for example in the shape of a hollow or solid egg, a hollow or solid cylinder, a tuboid or a hollow or solid tube, a spheroid or a hollow or solid sphere, or of monolayers partially folded back on themselves (2.5 D). It is the external layer of the microtissue or the layer of extracellular matrix, when this is present, which confers its size and its shape to the microtissue. An example of a solid microtissue is the cardiac spheroid used in bioproduction (https://doi.org/10.1016/j.bbamcr.2015.11.036).

According to an embodiment of the invention, the microtissue may be a human or animal biological microtissue intended to be grafted in humans or animals.

During implementation of the method, the microtissue may be realized on a living frozen or non-frozen microtissue.

The method according to the invention comprises the characterization of the microtissue by imaging, by a phase measurement technique without a reference beam.

Preferably, it is important to manage the coherence of the beam used for the lighting. In particular, it is expedient for the coherence in the region of the microtissue, i.e. that of the speckle generated by the sample (microtissue), to be reduced—preferably the speckle contrast is less than 75% of the unit contrast, yet more preferably 50%, ideally 10%. In practice, this reduction of the speckle is achieved by reducing the spatial coherence and/or the temporal coherence. The spatial coherence of the lighting should preferably be such that the digital illumination opening does not exceed 90%, yet more preferably 75%, ideally 50%, of the digital opening of the imaging system, so as to measure the parameters of the sample (microtissue) in a manner independent of the coherence of the beam.

According to a particularly suitable embodiment, the method is implemented using a spatially semi-coherent beam, i.e.:

- the spectral width of the source, i.e. the spectral range of the illumination, also referred to as the illumination wavelength (corresponds to the temporal coherence of the illumination) is at least 5 nm in the visible, and at most 600 nm; ideally approximately 100 nm, for example 100 nm; and
- the digital illumination opening (corresponding to the spatial illumination coherence) is at least 5% and at most 90% of the digital opening of the imaging system, ideally approximately 50%, for example 50%.

This feature makes it possible in particular to guarantee a quantitative phase measurement that is comparable, whatever the sample (microtissue) and the illumination, while measuring the parameters of the microtissue in its entirety.

Preferably, the phase measurement technique without a reference beam is selected from:

- wavefront analysis
- the dynamic modulation of the phase or of the luminous intensity in the pupil of the illumination or imaging system
- the multiple imaging of luminous intensity with modification of the focusing plane.

When the phase measurement technique without a reference beam is wavefront analysis, it is preferably performed by means of imaging of gradients of the wavefront, and in particular a wavefront gradient imaging technique selected from:

- the Shack-Hartmann method (Gong, H. et al. *Optical path difference microscopy with a Shack Hartmann wavefront sensor*. Opt. Lett. (2017) oi:10.1364/OL.42.002122),
- the modified (or unmodified) Hartmann method (Bon, P., Maucort, G., Wattellier, B. & Monneret, S. *Quadriwave lateral shearing interferometry for quantitative phase microscopy of living cells*. Opt. Express 17, 13080-13094 (2009)),
- partitioning of the pupil (Parthasarathy, A. B., Chu, K. K., Ford, T. N. & Mertz, J. *Quantitative phase imaging using a partitioned detection aperture*. Opt. Lett. 37, 4062-4064 (2012)),
- speckle field imaging (Berto, P., Rigneault, H. & Guillon, M. *Wavefront sensing with a thin diffuser*. Opt. Lett. 42, 5117-5120 (2017)).

Preferably, the phase measurement technique without a reference beam, used in the method according to the invention, is the modified Hartmann method, because this is the technique which makes it possible to achieve the best compromise in terms of stability, sensitivity and compactness, for the characterization of microtissues.

When the phase measurement technique without a reference beam is the dynamic modulation of the phase or of the luminous intensity in the pupil of the illumination or imaging system, it is preferably performed by means of:

- ptychography (Zheng, G., Horstmeyer, R. & Yang, C. Wide-field, high-resolution Fourier ptychographic microscopy. Nat. Photonics 7, 739 (2013)), or
- the selective phase modulation of certain frequencies in the pupil (Wang, Z. et al. Spatial light interference microscopy (SLIM). Opt. Express 19, 1016-1026 (2011)).

Preferably, the phase measurement technique without a reference beam, used in the method according to the invention, is the ptychography technique, because the phase quantification there is more direct than the selective phase modulation, which provides images that are only slightly quantitative.

When the phase measurement technique without a reference beam is the multiple imaging of luminous intensity with modification of the focusing plane, it is preferably performed by means of:

- simultaneous multiplane imaging (Descloux, A. et al. Combined multi-plane phase retrieval and super-resolution optical fluctuation imaging for 4D cell microscopy. Nat. Photonics 12, 165-172 (2018)) or sequential multiplane imaging (Soto, J. M., Rodrigo, J. A. & Alieva, T. *Label-free quantitative 3D tomographic imaging for partially coherent light microscopy*. Opt. Express 25, 15699-15712 (2017) or Barty, A., Nugent, K. A., Paganin, D. & Roberts, A. *Quantitative optical phase microscopy*. Opt. Lett. 23, 817-819 (1998)).

Preferably, the phase measurement technique without a reference beam, used in the method according to the invention, is the simultaneous technique, because it is rapid, even if it is more complex than the sequential multiplane imaging.

Whatever the phase measurement technique without a reference beam, the method preferably comprises the measurement of the phase and optionally of the luminous intensity of the light that has passed through the microtissue.

Preferably, the method according to the invention is a method for in vitro characterization of a eukaryote biological microtissue by imaging by means of a phase measurement technique without a reference beam, said method comprising at least the study of the organization of cells in the microtissue, preferably at least the topology of the microtissue and/or the relative positioning of cells in the microtissue.

According to a preferred embodiment, the method comprises measuring:

- the density of the microtissue, from the phase measurement, and optionally the local absorption of the microtissue, from the phase measurement and the luminous intensity measurement of the light that has passed through the microtissue.

The density of the microtissue can be measured from the phase measurement as follows:

1) the zone of the image containing the microtissue (referred to as the useful zone) is separated from the remainder (referred to as the base, generally the culture medium);

2) the phase value of the base is subtracted from the phase of the useful zone;

3) following this subtraction, the phase is converted, if required, into the optical path difference (expressed in metric units) and added to the entirety of the useful zone;

4) said value is multiplied by the surface of an elementary pixel of the image, brought into the object plane—a value in cubic metric units is obtained;

5) said magnitude is divided by the specific refraction increment (Barer, *Interference microscopy and mass determination*, Nature, 1952) which is 0.18 $\mu m^3$/pg on average and which can be adjusted for each tissue—thus, a measurement of the "dry" mass is obtained (total mass—mass of culture medium), integrated over the entire sample (microtissue).

A comparison and description of this technique is available (Zangle, T. and Teitell, M. A., *Live-cell mass profiling: an emerging approach in quantitative biophysics*, Nature Methods, 2014).

The density is expressed in mass units (g).

The local absorption of the microtissue can be measured from the phase measurement and the luminous intensity measurement of the light that has passed through the microtissue, in the following manner. By means of a combined measurement of the phase φ and of the intensity I, the electromagnetic field is obtained $E=Ie^{i\varphi}$. Said complex magnitude can be broken down by extracting the real and imaginary part in the digital Fourier space of the electromagnetic field (via a Fourier transform). By returning to the direct space (via an inverse Fourier transform) of the real component, from the Fourier space, it is possible to go back to the component of the local absorption.

The measurement of the absorption is expressed in photon/$cm^2$.

Preferably, the method according to the invention comprises the measurement of at least one of the following parameters:

dimensions of the microtissue dimensions of at least one of the cells of the microtissue number of cells in the microtissue overall and local mass of the microtissue overall and local density of the microtissue distribution of mass in the microtissue organization of cells in the microtissue—topology of the microtissue and/or relative positioning of cells in the microtissue viability of cells of the microtissue texture.

The dimensions of the microtissue can be measured from the phase measurement as follows. The dimensions in the plane of the image are extracted by automatic trimming (edge detection algorithm of the Otsu type for example, or manual trimming), and the dimensions obtained by an adjustment of the trimming by an ellipsis (in the case of an egg-shaped microtissue).

The dimensions are expressed in micrometers.

The dimensions of one or more cell(s) of the microtissue can be measured from the phase measurement as follows. When the optical resolution is better than the size of a cell, manual or automatic trimming within the microtissue is performed (edge or watershed detection algorithm). The dimensions are then obtained by an adjustment of each automatic trimming by an ellipsis.

The dimensions of a cell are expressed in micrometers.

The overall mass of the microtissue can be measured from the phase measurement as follows. The sum of the phase information (within the meaning of the optical path, expressed in μm) over the zone containing the microtissue (obtained by automatic or manual trimming) is then multiplied by the surface of a phase pixel returned into the space of the object (expressed in $\mu m^2$), then multiplied by the specific increment (generally 0.18 pg/μm3) in order to obtain the overall mass measurement.

The overall mass is expressed in micrograms.

The local mass of the microtissue can be measured from the phase measurement as follows. The same method as for the above point is applied, but adding the phase only over a selected portion of the microtissue.

The local mass is expressed in micrograms.

The overall density of the microtissue can be measured from the phase measurement as follows. The mass is measured from the phase. The transverse dimensions in the image plane are obtained with the phase image. The dimension in the orthogonal plane of the image phase (referred to as thickness) is obtained: a) by a 3D reconstruction of the object in different imaging planes, b) or by a hypothesis on the shape of the object (generally egg-shaped), c) or by a hypothesis on the average optical refraction index of the microtissue and of the medium which makes it possible, by dividing the phase (within the meaning of the optical path difference) by the difference in the refractive index, to trace back to the thickness of the microtissue. The three dimensions are combined in order to obtain the volume of the sample (microtissue). By dividing the mass by the volume, the volume mass is returned.

The overall density is expressed in $g/cm^3$.

The local density of the microtissue can be measured from the phase measurement as follows. The same protocol as for the measurement of the overall density is used, but limiting the measured zone to a portion of the microtissue. The local density is expressed in $g/cm^3$.

The distribution of mass in the microtissue can be measured from the phase measurement as follows. Local mass measurements are carried out on sub-portions of the microtissue covering all or some of the microtissue. A statistical analysis of its masses (standard deviation, mean/median type) is performed.

The mass distribution is expressed in grams.

The organization of cells in the microtissue is to be taken within the histological meaning of the term, as understood by a person skilled in the art, and denotes the topology of the tissue and the relative positioning of the cells and the elements of the extracellular matrix. The viability of cells of the microtissue can be measured from the phase measurement as follows: local mass measurements are carried out on the sub-portions of the microtissue covering all or some of the microtissue. A statistical analysis of its masses (standard deviation, mean/median type) is performed.

The mass distribution is then correlated to a conventional histological analysis in order to generate an analyzed and annotated training dataset. Algorithm-based and/or directed machine learning (neural network type for example) can then be performed on this set of data, in order to automate the method.

The organization of cells in the microtissue is thus qualified by an expert system, human or otherwise, based on the histological classification.

The phenomena of cell death cause a change in the density and the size of the cells which can be detected in phase. The viability of cells of the microtissue can be measured from the phase measurement as follows: local mass measurements are carried out on the sub-portions of the microtissue covering all or some of the microtissue. A statistical analysis of its masses (standard deviation, mean/median type) is performed. The mass distribution is then correlated to conventional viability measurements such as ethidium bromide (dead cells) and calcein (living cells) identifying the percentage of living cells in order to generate an analyzed and annotated training dataset. Algorithm-based and/or directed machine learning (neural network type for example) can then be performed on this set of data, in order to automate the method.

The viability of the cells in the microtissue is thus expressed in percentage of living cells of the total cells.

The texture of the microtissue can be measured from the phase measurement as follows. The measurement of spatial variation statistics of the phase, including the standard deviation and frequency distribution of structures of the image within the region of interest, makes it possible to determine texture parameters.

The texture is expressed in phase units and in (phase unit)/μm.

According to an embodiment, the method according to the invention can be performed in vitro on microtissues which have been previously taken from a human, an animal, or a vegetable. The method may make it possible, for example, to characterize the quantity of an islet of Langerhans originating from the cadaver (in particular its viability) prior to a transplant in a diabetic patient, or indeed to characterize a pre-implantation embryo.

According to another embodiment, the method according to the invention can be performed in vitro on microtissues comprising pluripotent or progenitor stem cells intended to be differentiated, or on microtissues comprising cells undergoing differentiation, or on microtissues comprising differentiated cells obtained by cell culture from pluripotent or progenitor stem cells. The method according to the invention can be performed in vitro on microtissues made up of pluripotent or progenitor stem cells intended to be differentiated, or on microtissues made up of cells undergoing differentiation, or on microtissues made up of differentiated cells obtained by cell culture from pluripotent or progenitor stem cells.

Figure 3:
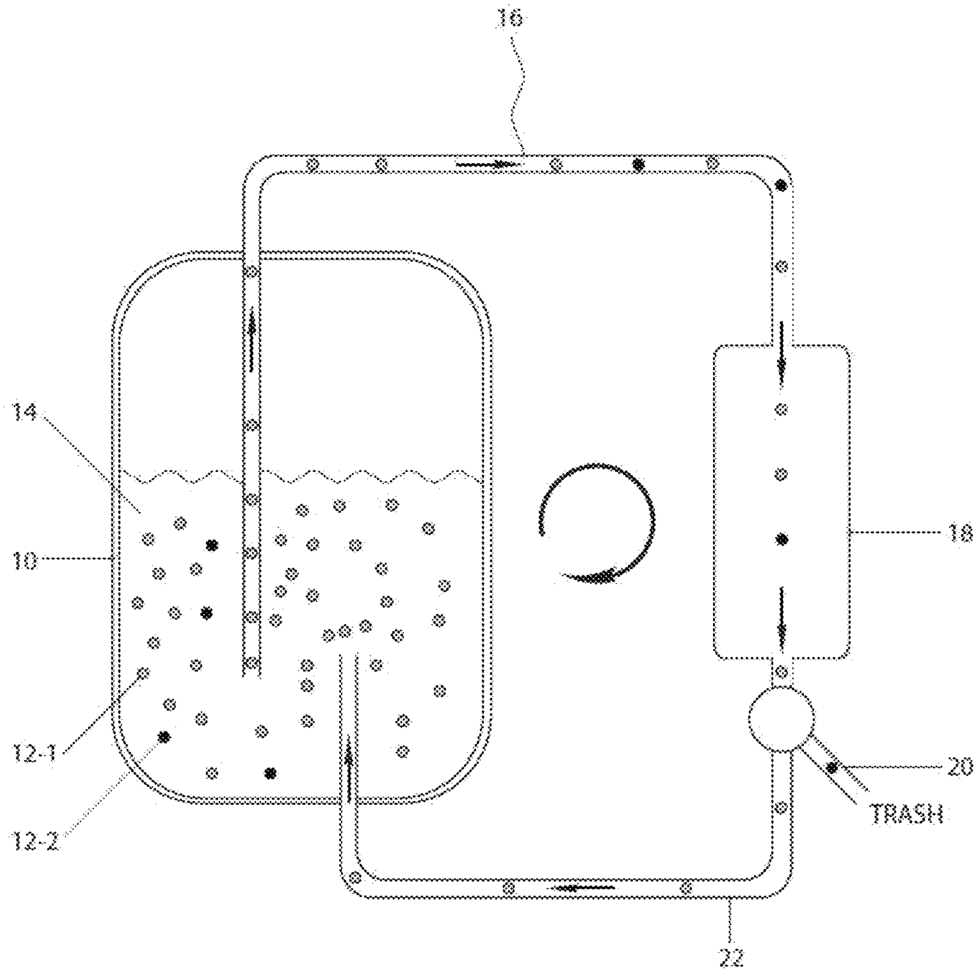
FIG. 3 is a schematic illustration of the implementation of a variant of the method online for characterizing biological microtissues contained in a bioreactor.

According to a variant, the method according to the invention is implemented online, on the contents of a bioreactor. An example of such a variant applied to the cell culture in capsules or microcompartments is shown in FIG. 3. In this example, capsules 12 each containing a microtissue are in suspension in a culture medium 14 in a bioreactor 10. Output means 16 arranged on the bioreactor make it possible to output the capsules 12 into their culture medium 14 and to cause them to pass into a phase measurement imaging system without a reference beam 18. At the output of said system 18, the capsules comprising microtissues which meet the quality criteria defined by the user of the bioreactor, referred to as normal capsules 12-1 in their culture medium 14, are reintegrated into the bioreactor 10 via input means 20, and the undesirable capsules 12-2, which do not meet the quality criteria defined by the user of the bioreactor, are recovered via elimination means 22 in order to be eliminated. The output means 16 can for example be a pipe and a peristaltic pump. The input means 20 can for example be a pipe. The elimination means 22 can for example be a piezoelectric valve system. The system 18 can be any imaging system capable of phase measurement without a reference beam, like the one described in the present application.

This advantageously makes it possible to verify the quality of the microtissues, in particular online, during differentiation or maturation. The method according to the invention, in particular in the context of implementation during differentiation or maturation of cells forming a microtissue in a bioreactor, can thus be performed:

i) in flow cells, i.e. by continuous recirculation of the content of a culture chamber of the bioreactor type within a sterile fluid system for purposes of analysis and/or sorting of the content of said culture chamber, or ii) in spot sampling outside of the bioreactor in order to analyze a part of said bioreactor at a particular point in time, typically during sampling for purposes of analysis and/or reseeding of a second bioreactor within the context of a "seed train," and/or within the context of an increase in volume and/or fragmentation of the content of the bioreactor in a plurality of quality control conditions or chambers, or iii) for sorting the microtissues offline during emptying of the bioreactor for purposes of purification or for pursuing a production and/or differentiation or conditioning sequence.

The method according to the invention has several advantages compared with the methods currently used. In particular, it can be implemented without destroying or modifying the microtissues studied, it is rapid to implement, requires simple equipment, and makes it possible to measure numerous physical parameters for characterizing the microtissues which was not possible using the methods of the prior art.

The method can thus be used for numerous applications. In particular, the invention relates to the use of the method, for:

monitoring the quality of a microtissue—indeed, the implementation of the method according to the invention makes it possible to measure characteristics of the microtissue, such as its size, its density, the number of cells, or its texture, which make it possible to verify the quality of a microtissue, and/or measuring the increase of the biomass of a microtissue during its growth and/or its amplification—indeed, the method according to the invention makes it possible to measure the overall or local mass of a microtissue, and thus makes it possible to follow the increase of the number of cells in a microtissue during its growth, its differentiation, and/or its amplification, and/or following the differentiation and/or the development of the topology of a microtissue in its maturation, and in particular the relative position in space of cells making it up—indeed, the method according to the invention makes it possible to measure the distribution of mass in the microtissue, and/or the organization of cells in the microtissue, and/or the viability of cells of the microtissue, during differentiation and/or maturation of cells of the microtissue, which provides information relating to the differentiation and/or the maturation of said cells, and/or determining the phenotype of cells of the microtissue—indeed, the method according to the invention makes it possible to measure the mass of each cell and the texture of the microtissue, which provides information relating to the phenotype of said cells, and/or confirming the absence of non-differentiated cells in the microtissue—indeed, measuring the mass of the cells and/or the density of the cells, the texture of the microtissue, and/or the organization of cells in the microtissue provide(s) information relating to the differentiation of cells of the microtissue, and consequently the possible absence of differentiation of said cells.

According to a particular embodiment, the microtissue may be an embryo. Thus, the method according to the invention can be used for screening embryos obtained by in vitro fertilization. The histological structure of a healthy embryo is typical, highly reproducible, and predictive of the success of the implantation of the embryo in the mother. In particular, in order to describe this structure on an embryo intended to be reimplanted, only solutions of imaging without marking are conceivable. In order to improve the yield of implantations and reduce the risk of failure, or, in contrast, of multiple embryos, clinics are developing ever more precise monitoring of the fertilized embryo in pre-implantation, in particular using video monitoring of the development. The method according to the invention makes it possible to more efficiently eliminate the embryos having an abnormal structure, by adding a relevant information source and without marking, and thus non-destructively.

According to another embodiment, the microtissue is a microtissue produced for the purpose of bioproduction of medicine or food.

The invention is now illustrated by way of an embodiment of the method according to the invention, compared with an example of a characterization method of the prior art.

EXAMPLES

Example 1

In this example, the method relates to the analysis of a human microtissue contained in a microcompartment, as described in example 1 of the application WO2018/096277 (example 1: protocol for obtaining cellular microcompartments from human cells induced to pluripotency).

Figure 2:
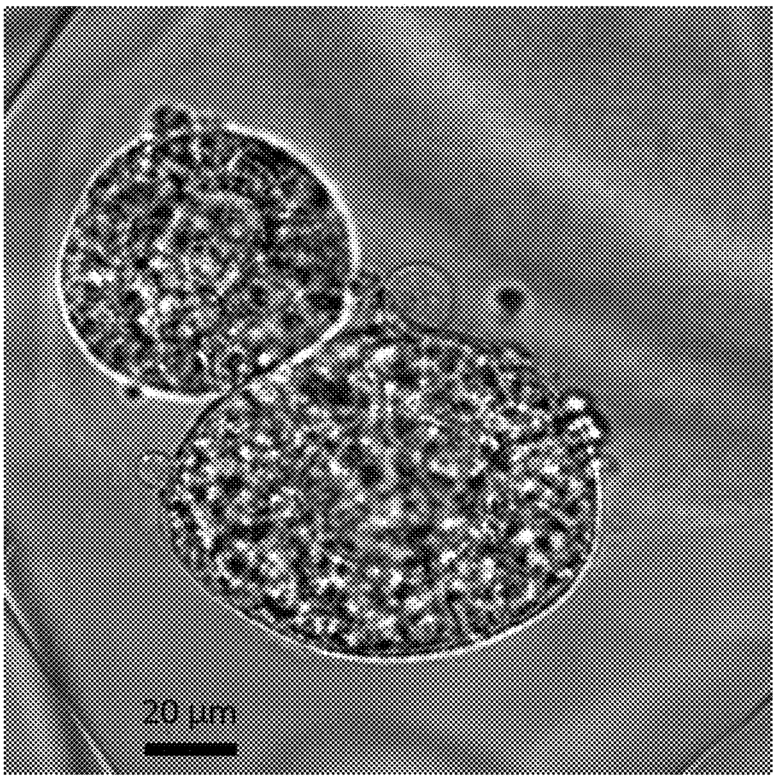
FIG. 2 is an image of hydrogel capsules containing human cells induced to pluripotency, obtained by imaging by phase intensity measurement (absolute measurement), according to the protocol described in the example.

A microcompartment has been analyzed according to an imaging process by measuring the intensity, as described in (Bon P. et al, *Quadriwave lateral shearing interferometry for quantitative phase microscopy of living cells,* 2009 Optical Society of America). The intensity has been obtained by demodulation of low frequencies via processing in the Fourier space of an interferogram obtained using the protocol set out in FIG. 4. The results obtained are set out in FIG. 2.

Figure 4:
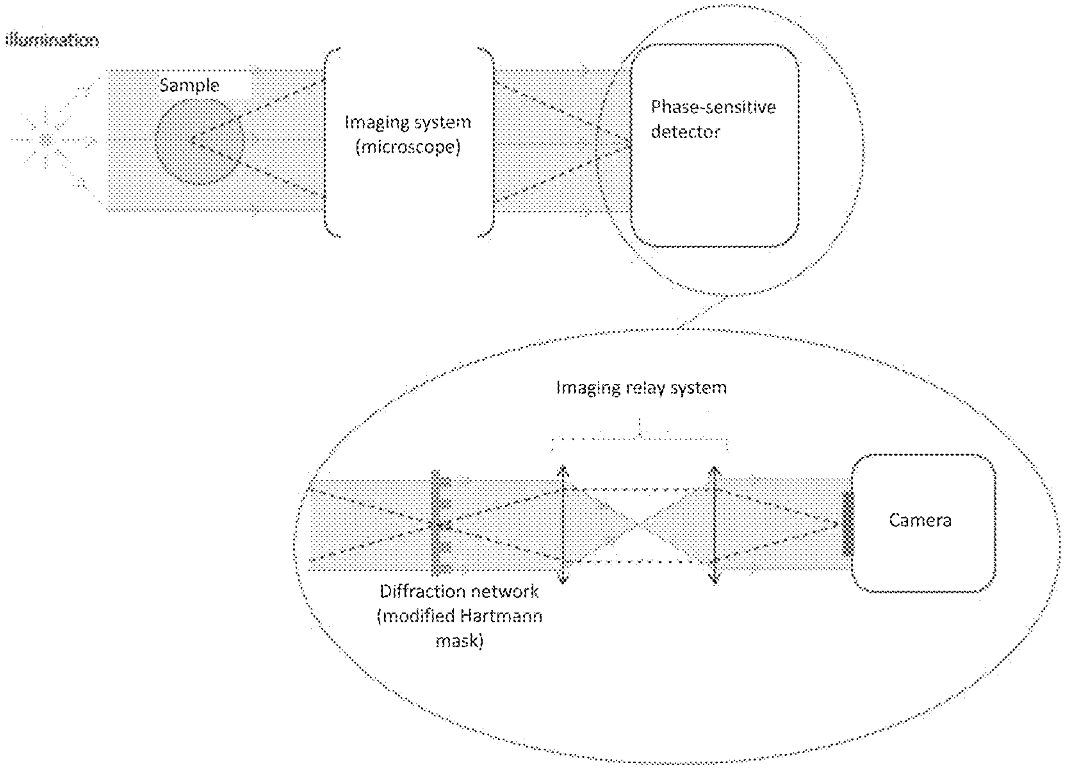
FIG. 4 is a schematic illustration of the imaging system for phase measurement without a reference beam, used for the characterization method according to the invention described in example 1.

A microcompartment was analyzed according to a method according to the invention. The operating protocol is described in the following: a halogen light is used for transmission illumination of the sample, a microscope objective (×20, digital opening 0.5) mounted on an inverted microscope is used for forming the image of the sample on a self-referenced interferometer (detector sensitive inter alia to the phase). The imaging technique used is the imaging of gradients of the wavefront, and in particular the modified Hartmann method. The protocol is also shown schematically in FIG. 4. FIG. 4 shows the illumination system, the sample, the microscope, and the phase-sensitive detector. A zoom is shown in order to describe the modified Hartmann assembly used for obtaining FIGS. 1 and 2.

The results obtained are set out in FIG. 1.

It is noted that the image obtained by means of the method according to the invention makes it possible to measure the local density of the sample and to decorrelate it from the absorption by comparison with the image obtained by the technique of the prior art. In particular, the method according to the invention has made it possible to measure:

the overall dimensions of each microtissue, which are 91 μm (for the largest) and 59 μm (for the smallest), and calculated by measuring the diameter, in pixels, of each microtissue on the image D. With knowledge of the total magnification of the imaging system $g_y$ and the physical size of a measuring pixel Tpix, the dimension of a microtissue is thus $D\times Tpix/g_y$.

the diameter of the light zone in the center of each microtissue by means of an analysis of the dimensions of the zone having a homogeneous granularity and a smaller phase shift (i.e. darker image) within the microtissue, measured at 38 μm for the largest microtissue and 25 μm for the smallest.

the dry mass of the object (the integral over the object of the volume mass), which is 39 μg for the largest microtissue and 16 μg for the smallest, calculated as described in the publication (Aknoun S. et al., Living cell dry mass measurement using quantitative phase imaging with quadriwave lateral shearing interferometry: an accuracy and sensitivity discussion, J/of Biomedical Optics, 2015). In short, it is a case of automatically trimming each microtissue by determining the edges, evaluating the base phase value by polynomial fit, extracting it from the image, summing all the phase information of each microtissue, and converting this into mass by means of the following equation: $m=0.18\ pg/\mu m^3\times\iint_{microtissue} phase\cdot ds$ the number of cells, which is 608±176 cells for the largest microtissue and 244±64 cells for the smallest microtissue. This value is obtained by two complementary approaches. With knowledge of the average size of a cell (5 μm) and the volume of the zone where there are cells in the microtissue (volume of microtissue—volume of the light), a value of the number of cells (respectively 421 and 180 cells) is deduced therefrom. With knowledge of the average mass of a stem cell (50 pg) and the total mass of the microtissue, another evaluation of the number of cells (respectively 784 and 312 cells) is deduced therefrom.

Example 2

In this example, the method relates to the analysis of a plurality of human microtissues contained in microcompartments, as described in example 1 of the application WO2018/096277 (example 1: protocol for obtaining cellular microcompartments from human cells induced to pluripotency). Pluripotent human stem cells (Gibco Human Episomal PSC) were encapsulated in an extracellular matrix surrounded by a porous wall of alginate and cultivated for 6 days in a growth medium in a growth medium (supplemented MTesr1).

The microtissues were analyzed according to the method according to the invention. The operating protocol is described in the following: a halogen light is used for transmission illumination of the sample, a microscope objective (×20 NA, digital opening 0.45) mounted on an inverted microscope is used for forming the image of the sample on a self-referenced interferometer (detector sensitive inter alia to the phase). The imaging technique used is quantitative phase imaging by interferometry. The protocol is also shown schematically in FIG. 4. The digital illumination opening is 0.13 (spatial coherence of the illumination), the illumination wavelength is 550±100 nm (spectral range of the illumination, or temporal coherence of the illumination).

Figure 5A:
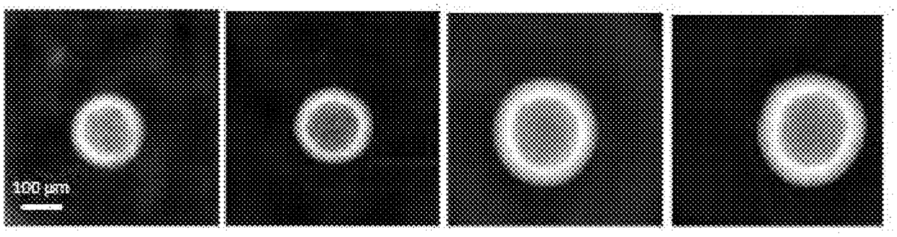
FIG. 5*a* shows images captured according to the method according to the invention of microtissues originating from the encapsulation of induced human stem cells (Gibco Human Episomal) in alginate capsules after 6 days of culture in a growth medium (supplemented MTesr1) according to the protocol of example 2. The microtissue is made up of stem cells forming a single cyst and/or complying with criteria of homogeneity of cell distribution and of roundness, allowing for their classification in the category of acceptable microtissues.
Figure 5B:
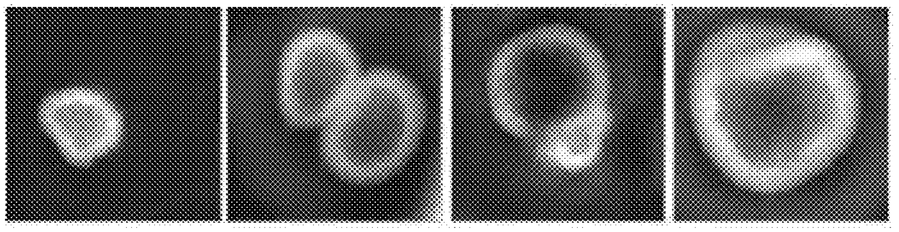
FIG. 5*b* shows images captured, according to the method according to the invention, of microtissues originating from the encapsulation of induced human stem cells (Gibco Human Episomal) in alginate capsules after 6 days of culture in a growth medium (supplemented MTesr1) according to the protocol of example 2. The microtissue is made up of stem cells forming a plurality of cysts and/or exhibiting an inhomogeneity of cell distribution and of roundness, allowing for their classification in the category of non-acceptable microtissues.
Figure 5C:
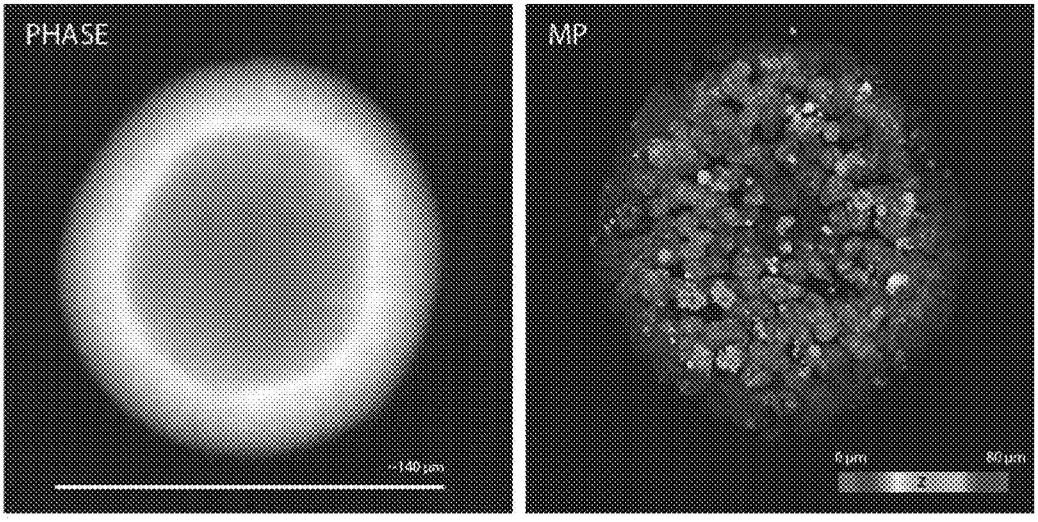
FIG. 5*c* (left-hand side) shows an image, captured according to the method according to the invention, of microtissues originating from the encapsulation of induced human stem cells (Gibco Human Episomal) in alginate capsules after 6 days of culture in a growth medium (supplemented MTesr1).

The results obtained are set out in FIGS. 5*a*, 5*b* and 5*c*. They make it possible to characterize the texture and the roundness of the microcompartments with microtissues which are acceptable (5*a*) and not acceptable (5*b*).

In FIG. 5*a*, the microtissues are made up of stem cells forming a single cyst and/or complying with criteria of homogeneity of cell distribution and of roundness, allowing for their classification in the category of acceptable microtissues.

In FIG. 5*b*, the microtissues are made up of stem cells forming a plurality of cysts and/or exhibiting an inhomogeneity of cell distribution and of roundness, allowing for their classification in the category of non-acceptable microtissues.

It is noted that the method according to the invention makes it possible, by means of statistical analysis of roundness and homogeneity of texture, to characterize the acceptable microtissues and the non-acceptable microtissues, even if dense.

FIG. 5*c* shows, on the left-hand side, a of a microtissue obtained according to the method of example 2, and, on the right-hand side, the same microtissues acquired by means of multiphotonic microscopy (the cell nuclei are marked by 10 ug/mL Hoechst 33342 (Thermofisher)). Approximately half of the cells are visible in multiphotonics, compared with the invention. The total number of cells is approximately 500.

It is also noted that the marking of the nuclei of cells of the microtissues makes it possible to correlate the data of the texture and the roundness with the number of cells.

Example 3

In this example, the method relates to the analysis of a human microtissue contained in a microcompartment, as described in example 1 of the application WO2018/096277 (example 1: protocol for obtaining cellular microcompartments from human cells induced to pluripotency) compared with the same microcompartment without microtissue.

The microcompartments with and without microtissues were analyzed according to the method according to the invention. The operating protocol is described in the following: a halogen light is used for transmission illumination of the sample, a microscope objective (×20 NA, digital opening 0.45) mounted on an inverted microscope is used for forming the image of the sample on a self-referenced interferometer (detector sensitive inter alia to the phase). The imaging technique used is quantitative phase imaging by interferometry. The digital illumination opening is 0.13 (spatial coherence of the illumination), the illumination wavelength is 550±100 nm (spectral range of the illumination, or temporal coherence of the illumination).

Figure 6:
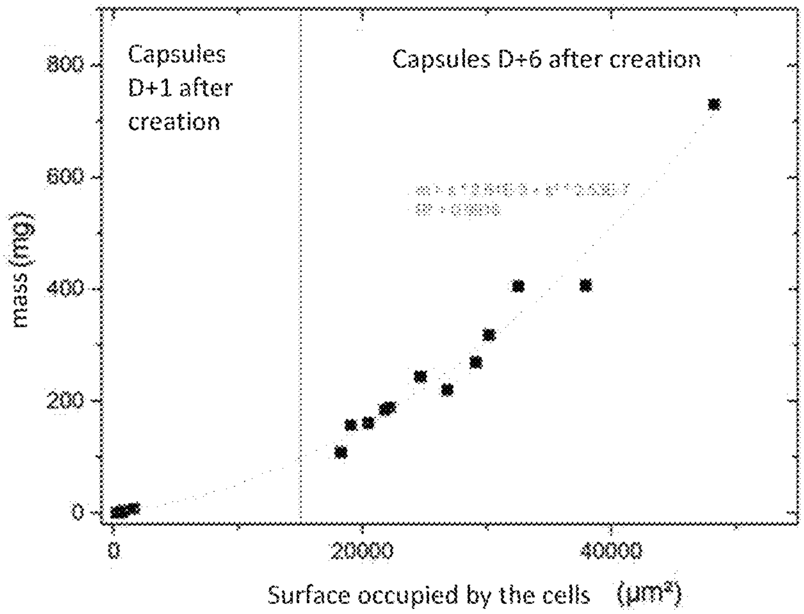
FIG. 6 is a graphical representation of comparative mass and surface measurement results between the microtissues of stem cells in alginate capsules at different times (1 to 6 days) after encapsulation, showing the quadratic growth of the mass and the diversity of mass and of maturity for the samples produced at the same time, according to example 2.
Figure 7:
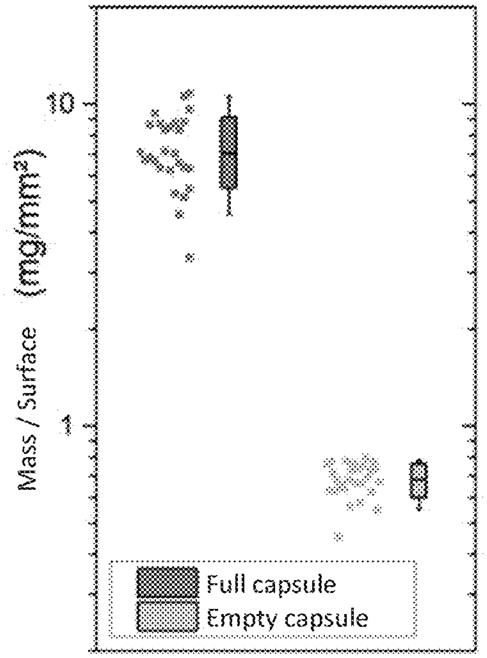
FIG. 7 is a graphical representation of comparative mass measurement results normalized at the surface between capsules containing microtissues and empty capsules, according to example 2.

The results obtained are set out in FIG. 6 and in FIG. 7.

FIG. 6 shows, perfectly, a quadratic development of the growth of cells, and a dispersion on a given date, in order to determine the growth of the population and select the mature microtissues.

It can be seen in FIG. 7 that the phase imaging makes it possible to characterize the density of the cells present in a microtissue.

The invention claimed is:

1. A method for in vitro characterization of a eukaryotic biological microtissue having a smallest dimension greater than or equal to 20 µm, the method comprising:

illuminating and imaging the eukaryotic biologic microtissue in real time by a phase measurement technique without a reference beam;

wherein a spectral range of illumination is at least 5 nm in the visible spectrum, and at most 600 nm; and a digital illumination opening is at least 5% and at most 90% of a digital opening of an imaging system; and wherein said illuminating and imagining in real time are performed without destroying or modifying said eukaryotic biological microtissue.

2. The method for in vitro characterization of a eukaryotic biological microtissue of claim 1, said method comprising at least a study of the organization of cells in the microtissue.

3. The method for in vitro characterization of a eukaryotic biological microtissue of claim 1, wherein the method comprises mapping organization of cells in the microtissue, including topology of the microtissue and/or a relative positioning of cells in the microtissue.

4. The method for in vitro characterization of a eukaryotic biological microtissue of claim 1, characterized in that a speckle contrast generated by the microtissue is less than 75% of a maximum unit contrast.

5. The method for in vitro characterization of a eukaryotic biological microtissue of claim 1, the microtissue being a human, animal or vegetable microtissue.

6. The method for in vitro characterization of a eukaryotic biological microtissue of claim 1, characterized in that a largest dimension is less than or equal to 10 mm.

7. The method for in vitro characterization of a eukaryotic biological microtissue of claim 1, characterized in that the phase measurement technique without a reference beam is selected from:

wavefront analysis dynamic modulation of a phase or of a luminous intensity in a pupil of the illumination or imaging system multiple imaging of luminous intensity with modification of a focusing plane.

8. The method for in vitro characterization of a eukaryotic biological microtissue of claim 1, characterized in that the phase measurement technique without a reference beam is wavefront analysis, and in that the method is performed by means of imaging of gradients of the wavefront analysis.

9. The method for in vitro characterization of a eukaryotic biological microtissue of claim 8, characterized in that the imaging of gradients of the wavefront analysis is selected from the Shack-Hartmann method, the modified or unmodified Hartmann method, a positioning of a pupil, and speckle field imaging.

10. The method for in vitro characterization of a eukaryotic biological microtissue of claim 1, characterized in that the phase measurement technique without a reference beam is dynamic modulation of a phase or of luminous intensity in a pupil of the illumination or imaging system, and in that the method is performed using ptychography technique or a technique of selective phase modulation of certain frequencies in the pupil.

11. The method for in vitro characterization of a eukaryotic biological microtissue of claim 1, characterized in that the phase measurement technique without a reference beam is multiple imaging of luminous intensity with modification of a focusing plane, and in that the method is performed by means of simultaneous or sequential multiplane imaging.

12. The method for in vitro characterization of a eukaryotic biological microtissue of claim 1, characterized in that the method comprises a measurement of a phase and optionally of a luminous intensity of light that has passed through the microtissue.

13. The method for in vitro characterization of a eukaryotic biological microtissue of claim 1, characterized in that the method comprises a measurement of:

a density of the microtissue, from a phase measurement, and optionally local absorption of the microtissue, from the phase measurement and a luminous intensity measurement of light that has passed through the microtissue.

14. The method for in vitro characterization of a eukaryotic biological microtissue of claim 1, characterized in that the method comprises a measurement of at least one of the following parameters:

dimensions of the microtissue,
dimensions of at least one of cells of the microtissue,
number of cells in the microtissue,
overall and local mass of the microtissue,
overall and local density of the microtissue,
distribution of mass in the microtissue,
topology of the microtissue,
relative positioning of cells in the microtissue,
viability of cells of the microtissue, and/or
texture of the microtissue.

15. The method for in vitro characterization of a eukaryotic biological microtissue of claim 1, characterized in that the microtissue is encapsulated in a microcompartment comprising an external hydrogel layer.

16. The method for in vitro characterization of a eukaryotic biological microtissue of claim 1, characterized in that the microtissue is in the shape of an egg, a tube, a spheroid, or a sphere, or of monolayers partially folded back on themselves.

17. The method for in vitro characterization of a eukaryotic biological microtissue of claim 1, characterized in that the microtissue is surrounded, at least in part, by an extracellular matrix.

18. The method for in vitro characterization of a eukaryotic biological microtissue of claim 1, characterized in that the microtissue is a human or animal biological microtissue graft suitable for grafting in humans or animals after completion of the imaging by means of the phase measurement technique.

19. The method for in vitro characterization of a eukaryotic biological microtissue of claim 1, characterized in that the microtissue is a human or animal biological microtissue selected from epithelial, connective, muscular or nerve microtissues.

20. The method for in vitro characterization of a eukaryotic biological microtissue of claim 1, characterized in that the microtissue comprises differentiated cardiac cells or retinal cells or neural cells or cells of the liver or chondrocytes or keratinocytes or lymphoid cells, or hematopoietic stem cells or mesenchymal stem cells or pluripotent cells in the form of an epiblast.

21. The method for in vitro characterization of a eukaryotic biological microtissue of claim 1, characterized in that the microtissue is a medicine or food product.

22. The method for in vitro characterization of a eukaryotic biological microtissue of claim 1, characterized in that the microtissue is a vegetable biological microtissue selected from meristems, parenchyma, conducting tissues, supporting tissues, covering or protective tissues, secretion tissues, and/or nutritive tissues.

23. The method for in vitro characterization of a eukaryotic biological microtissue of claim 1, characterized in that the method is performed online on the content of a bioreactor.

24. The method for in vitro characterization of a eukaryotic biological microtissue of claim 1, characterized in that the method is performed:

i) in flow cells, or
ii) in spot sampling outside of a bioreactor, or
iii) in order to separate the microtissues online or offline.

25. The method for in vitro characterization of a eukaryotic biological tissue of claim 1, wherein the method comprises one or more of the following:

monitoring a quality of the microtissue, and/or measuring an increase of a biomass of the microtissue during its growth and/or its amplification, and/or following differentiation and/or organization of the microtissue during its maturation, and/or determining a phenotype of cells of the microtissue, and/or confirming the absence of non-differentiated cells in the microtissue, and/or determining a viability of cells of the microtissue.

26. A method for screening an embryo obtained by in vitro fertilization, wherein the method comprises performing the method of claim 1, and wherein the embryo is the microtissue.

* * * * *